United States Patent [19]
Amiet et al.

[11] Patent Number: 4,595,541
[45] Date of Patent: Jun. 17, 1986

[54] PROCESS FOR THE PREPARATION OF TRIFLUOROACETIC ANHYDRIDE

[75] Inventors: Louis Amiet; Camille Disdier, both of Lyons, France

[73] Assignee: Rhone Poulenc Specialties Chimiques, France

[21] Appl. No.: 741,630

[22] Filed: Jun. 5, 1985

[30] Foreign Application Priority Data

Jun. 13, 1984 [FR] France .................. 84 09188

[51] Int. Cl.$^4$ .............................. C07C 51/56
[52] U.S. Cl. ................................... 260/546
[58] Field of Search .......................... 260/546

[56] References Cited

U.S. PATENT DOCUMENTS 1,863,788  6/1932  Hale ..................... 260/546
2,411,567  11/1946  Wotherspoon ............ 260/546

OTHER PUBLICATIONS

Randles, J. E. B. et al., *J. Chem. Soc.* (1954), pp. 436–441.
Noller, Carl R., *Chemistry of Organic Compounds* (1957) 2nd Ed., W. B. Saunders Company, Publ., pp. 162–163.
*CRC Handbook of Chemistry and Physics*, 60th Ed. (1979–80), CRC Press, Publ., pp. C-82, C-86, C-89, C-91, C-92 and C-98.

*Primary Examiner*—Natalie Trousof
*Assistant Examiner*—L. Hendriksen
*Attorney, Agent, or Firm*—Finnegan, Henderson, Farabow, Garrett & Dunner

[57] ABSTRACT

The present invention relates to a process for the preparation of trifluoroacetic anhydride which comprises bringing together trifluoroacetic acid with the anhydride of an α-halogenated acid.

16 Claims, No Drawings

PROCESS FOR THE PREPARATION OF TRIFLUOROACETIC ANHYDRIDE

The present invention relates to a process for the preparation of trifluoroacetic anhydride and, more particularly, to a process for the preparation of trifluoroacetic anhydride by exchange between trifluoroacetic acid and an acid anhydride.

It is known to prepare trifluoroacetic anhydride (Hudlicky, Chemistry of Organic Fluorine Compounds, 1976, p. 726) by reaction of trifluoroacetic acid with phosphoric anhydride. This method of preparation is very difficult to exploit industrially because the solid phase consisting of phosphoric anhydride tends to form amalgams interfering with the total recovery of the unconverted trifluoroacetic acid at the end of the reaction. Since trifluoroacetic acid is a very costly product, any loss is to be avoided.

It is also known according to Japanese Patent Application No. 70/38,523 to prepare trifluoroacetic anhydride by reaction of trifluoroacetyl chloride with an alkali metal or alkaline-earth metal salt of trifluoroacetic acid at approximately 50° C. This process is also very difficult to exploit industrially because trifluoroacetyl chloride is not a product which is generally available on the market and its price is consequently very high; furthermore, it is gaseous and difficult to employ; in addition, the trifluoroacetic anhydride formed is difficult to separate from sodium chloride formed as a by-product.

It is also known according to the European Patent Application published under No. 4641 to prepare acid anhydrides of the formula

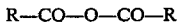

in which R can be $CF_3$, by condensation of the acid RCOOH and acetic anhydride at atmospheric pressure. This patent application does not describe any example of preparation of trifluoroacetic anhydride. In fact, when this procedure is followed with the use of trifluoroacetic acid as the acid, no trifluoroacetic anhydride is obtained in practice because the stoichiometric proportions of the starting products employed do not make it possible to displace the mixed anhydride formed, namely, $CF_3COOCOCH_3$, which is extremely stable.

In the face of all these technical and economic problems it has been desired to find an economical process easy to use to obtain trifluoroacetic anhydride. It is an object of the present invention to make it possible to attain this objective and the subject of the present invention is a process for the preparation of trifluoroacetic anhydride, in which trifluoroacetic acid is reacted with the anhydride of an α-halogenated acid.

The α-halogenated acid anhydrides preferably correspond to the following formula (I)

in which:

$Y_1$, $Y_2$ and $Y_3$ may be identical or different and are selected from chlorine, bromine and hydrogen;

n is an integer equal to 1 or 2; and at least one of the Y atoms situated at a position α to the CO group is a halogen selected from chlorine and bromine.

Among the anhydrides corresponding to formula (I) are included mono, di and trichloroacetic, mono, di and tribromoacetic, α-monochloropropionic, α, α-dichloropropionic, α, α, β-trichloropropionic, α-monobromopropionic, and α, α-dibromopropionic anhydrides, as well as mixed anhydrides of the chlorobromoacetic or chlorobromopropionic type.

It is preferred to use chloroacetic anhydrides in which n=1 and Y is selected from hydrogen and chlorine because these are most readily available, and more particularly dichloroacetic anhydride because under the reaction conditions this is the most thermally stable and the most economical of the above anhydrides.

For best yields to be obtained, the reaction is preferably carried out in the presence of an excess of trifluoroacetic acid relative to the stoichiometry of the reaction. The total quantity of trifluoroacetic acid is preferably between about 2 and 5 times the stoichiometry and more particularly approximately 4 times the stoichiometry.

The reaction may be carried out at a temperature higher than the boiling point of the reaction mixture. The reaction is preferably carried out at the boiling point of the mixture of trifluoroacetic acid and the α-halogenated acid anhydride and at atmospheric pressure, so as to distill off the trifluoroacetic anhydride formed. Since trifluoroacetic anhydride has a boiling point of 39.5° C., it can be readily distilled off continuously from the mixture. Thus, according to a particularly preferred embodiment of the invention, the temperature of the mixture is maintained between about 80° and 115° C.

When the distillation is completed the temperature is raised gradually so as to recover first the excess trifluoroacetic acid, the boiling point of which is 71° C., and then dichloroacetic acid, a by-product of the reaction.

According to a first embodiment, the α-halogenated acid anhydride is prepared by reaction of an excess of a halide of this acid with acetic anhydride. The acid halide is preferably selected from acid chlorides or bromides and more particularly from acid chlorides. The reaction is advantageously facilitated when the excess acid halide is at least about 25% relative to the stoichiometry.

According to this first embodiment of the invention, the α-halogenated acid halide is brought into contact with acetic anhydride preferably in a first step, the acetyl chloride formed and then the excess α-halogenated acid chloride are separated off, and in a second step the remaining mixture is brought into contact with trifluoroacetic acid and the trifluoroacetic anhydride produced is distilled off.

According to a second embodiment of the invention, the α-halogenated acid anhydride can be prepared by reaction of an α-halogenated acid with acetic anhydride. In this case, when the operation is carried out in the presence of an excess of α-halogenated acid, the yield of the α-halogenated acid anhydride is frequently relatively low.

According to this second embodiment of the invention, it is preferred to conduct the first step in preparation of the α-halogenated acid anhydride, as described in German Patent DE No. 1,100,612, in the presence of a solvent which is chemically inert under the reaction conditions, which has a boiling point higher than that of acetic acid or which forms with acetic acid an azeotrope having a boiling point lower than that of acetic acid. This solvent facilitates continuous distillation of the acetic acid formed, which makes it possible to increase the yields of α-halogenated acid anhydride.

Chlorobenzene and toluene are suitable as the solvent. The use of chlorobenzene is more particularly preferred.

Preferably, the solvent is present in an amount by weight, relative to the acetic anhydride employed, which is greater than about 500 grams per mole of anhydride and especially between about 500 and 2,000 grams per mole. The α-halogenated acid is employed in a slight excess relative to the stoichiometry and preferably in a quantity of between about 1 and 1.1 times the stoichiometry.

In the second step, the mixture originating from the first step is brought into contact with trifluoroacetic acid and the trifluoroacetic anhydride produced is distilled off.

The trifluoroacetic anhydride produced by the process according to the invention may be employed as a synthesis intermediate in the pharmaceutical or plant-protection industry.

The present invention will be understood more readily with the aid of the following examples, which are given by way of the indication without any restriction being implied.

EXAMPLE 1

Into a 1-liter round-bottomed glass laboratory flask, fitted with a 20-plate glass plate distillation column, there were charged 456 grams of technical trade trifluoroacetic acid (containing at most 0.3% of water), which corresponds substantially to 4 moles, followed by 120 grams, i.e. 0.5 mole, of pure dichloroacetic anhydride, which corresponds to a trifluoroacetic acid/dichloroacetic anhydride molar ratio of 8. The mixture was heated under total reflux at atmospheric pressure. The temperature at the head of the column gradually rose to 39°–39.5° C. After approximately 1 hour the condensed liquid was collected while a reflux ratio of approximately 20 was maintained, and while the temperature remained at 39°–39.5° C. The collection was stopped when the temperature began to increase rapidly, the fraction being separated off at 40° C. In this way, 70.5 grams of a product identified as trifluoroacetic anhydride $(CF_3CO)_2O$ by infrared spectrometry were collected over 2 hours 30 minutes. The weight collected corresponds to 0.335 mole, which represents a fraction of the initial dichloroacetic anhydride converted equal to 0.67.

EXAMPLE 2

The operating procedure of Example 1 was repeated, with the same number of moles of reactants, but with successive use of the anhydrides $(CH_3CO)_2O$, $(CH_2ClCO)_2O$ and $(CCl_3CO)_2O$ in the place of $(CCl_2HCO)_2O$. The fractions, determined as in Example 1, of each of these anhydrides which was converted to trifluoroacetic anhydride were found, respectively, to have the following values: 0.36–0.59–0.74.

EXAMPLE 3

Into a 3-liter round-bottomed flask supporting a glass plate distillation column were introduced 774 grams (6 moles) of anhydrous $CHCl_2COOH$ and 204 grams (2 moles) of acetic anhydride. The temperature of the mixture was raised to 140° C. and then acetic acid was distilled off at a temperature of 90° C. under a pressure reduced to 300 mm Hg. In this way 130 grams, i.e. 2.16 moles, of acetic anhydride were separated off. While the pressure was gradually reduced, a fraction consisting substantially of acetic anhydride was distilled off. The pressure was reduced further to approximately 20 mm Hg and a 500 gram fraction of $CHCl_2COOH$ (3.88 moles) was distilled off at a temperature of 100° to 105° C. at the head of the column, the undistilled residue thus corresponding to a production of approximately 1.06 mole of dichloroacetic anhydride.

The reaction flask was cooled to approximately 50° C., and then 1,140 grams of pure distilled $CF_3COOH$ (10 moles) were added, corresponding to a trifluoroacetic acid/dichloroacetic anhydride molar ratio of 9.4. The mixture was heated under reflux. The temperature at the head of the column was 39.5° C., which corresponds to the boiling point of $(CF_3CO)_2O$. After approximately 5 hours distillation, 178.5 grams, i.e. 0.85 mole, of $(CF_3CO)_2O$ had been collected (chemical nature verified by F-NMR spectrometry analysis). The distillation was contined. The temperature rose to 71° C., corresponding to the distillation of $CF_3COOH$. When the temperature reached 120° C. in the boiler and no further reflux was observed, heating was stopped. The $CF_3COOH$ fraction which was separated off weighed 911 grams (7.99 moles). The distillation residue consisted substantially of $CHCl_2COOH$. The yield of trifluoroacetic anhydride based on the trifluoroacetic acid consumed was 84.6%.

EXAMPLE 4

441 Grams, i.e. 3 moles, of $CHCl_2COCl$ were introduced into a 1-liter round-bottomed flask with a column and equipment required for distillation and fitted with a dropping funnel. The material was heated to 100° C. and then 102 grams (i.e. 1 mole) of acetic anhydride were added through the dropping funnel over approximately 1 hour 30 minutes. Heating was continued and acetyl chloride was distilled off at 50°–51° C. at the head of the column. In this way 141 grams of acetyl chloride (i.e. 1.796 moles) were separated off, which corresponds to a production of approximately 0.90 mole of dichloroacetic anhydride, then the pressure was reduced and a fraction containing principally the excess $CHCl_2COCl$ and a small amount of acetyl chloride not separated off with the first fraction, was distilled off. In this way 137 grams were collected.

Heating was stopped, the mixture was cooled to 40° C. and then 684 grams, i.e. 6 moles, of pure distilled $CF_3COOH$ were added, corresponding to a trifluoroacetic acid/dichloroacetic anhydride molar ratio of 6.6. The mixture was heated under reflux again. The procedure was as in the preceding example for the production of $(CF_3CO)_2O$ and 154 grams (i.e. 0.733 mole) of this product were collected. Then, a 474 gram fraction of excess $CF_3COOH$ (4.15 moles) and a 254 gram fraction of $CHCl_2COOH$ (1.96 moles) were separated off in succession.

There remained a residue of 33 grams. The yield of trifluoroacetic anhydride based on the trifluoroacetic acid consumed was 79.2%.

EXAMPLE 5

The procedure was as in Example 4.

First step: 3 Moles of $CHCl_2COCl$ (a 50% excess) were introduced for each 1 mole of acetic anhydride. There were collected:

(a) 140 grams of acetyl chloride, corresponding to an 89% conversion of acetic anhydride to acetyl chloride; and (b) 140 grams of excess $CHCl_2COCl$ containing a small amount of acetyl chloride.

Second step: 8 Moles of $CF_3COOH$ (912 grams) were introduced, corresponding to a trifluoroacetic acid/dichloroacetic anhydride molar ratio of 9. 168 Grams of $(CF_3CO)_2O$, i.e. 0.8 mole, were collected followed by 706 grams of excess $CF_3COOH$ (6.19 moles) and then 238 grams of a distillate of $CHCl_2COOH$ (1.846 moles). The residue weighed 33 grams.

The yield of trifluoroacetic anhydride based on the trifluoroacetic acid consumed was 88%.

EXAMPLE 6

The procedure was as in the preceding example with the following exception.

First step: only 2.6 moles of $CHCl_2COCl$ were introduced for each 1 mole of acetic anhydride.

After the reaction, there were separated off by distillation, 134 grams (1.707 moles) of acetyl chloride, corresponding to a conversion to $(CHCl_2CO)_2O$ of 85.3%, and then 101 grams containing substantially the excess $CHCl_2COCl$, which would correspond to 0.687 mole.

Second step: there were introduced 4 moles of $CF_3COOH$, i.e. 456 grams, corresponding to a trifluoroacetic acid/dichloroacetic anhydride molar ratio of 4.7. Over 6 hours there were collected by distillation 148 grams, i.e. 0.704 mole, of $(CF_3CO)_2O$, then 227 grams of $CF_3COOH$ (1.99 moles) and 187 grams of $CHCl_2COOH$, i.e. 1.45 moles.

The residue amounted to 45 grams.

The yield of trifluoroacetic anhydride based on the trifluoroacetic acid consumed was 70%.

EXAMPLE 7

Into a 2-liter round-bottomed flask equipped with a distillation column with 10 glass plates were introduced 1,000 grams of dry monochlorobenzene, 102 grams of pure acetic anhydride (i.e. 1 mole) and 284 grams of pure dichloroacetic acid (i.e. 2.2 moles).

The mixture was heated under total reflux and it was found that the temperature at the head of the column quickly stabilized at 112°–113° C. Distillation was then carried out at this temperature over 7 hours and 205 grams of a mixture were obtained; analysis showed that the $CH_3COOH$ content of this mixture was 52% (106.6 grams). Subsequently, over a little under 1 hour, a fraction, ranging from 113° C. at the start to 128° C. at the end, and weighing 48 grams was distilled off, containing, according to analysis, 10.9% of $CH_3COOH$, i.e. 5.2 grams.

The total quantity of $CH_3COOH$ separated off from the reaction mixture was 111.8 grams, corresponding to a $(CH_3CO)_2O$ conversion of approximately 93%.

The flask was cooled to approximately 40° C., and then 456 grams of pure anhydrous $CF_3COOH$ (i.e. 4 moles) were introduced. The materials were then heated under reflux. The temperature in the boiler rose to 105° C., and that at the head of the column became steady at 38.5°–39.5° C. 152 Grams of $(CF_3CO)_2O$ were distilled off over 6 hours, and then the reaction stopped. Cooling was then applied, 456 grams of pure anhydrous $CF_3COOH$ were added again and the distillation was restarted in the same manner as after the first addition. At the end of the distillation, the boiler temperature reached 90° C. An additional 52 grams of $(CF_3CO)_2O$ were distilled off over approximately 2 hours.

The total quantity of trifluoroacetic anhydride recovered was thus 204 grams, i.e. 0.97 mole.

The excess $CF_3COOH$ was then distilled off and in this way 646 grams of this acid, i.e. 5.67 moles, were recovered. The boiler temperature was then 136° C. The consumption of $CF_3COOH$ had thus become (8−5.67) moles, i.e. 2.33 moles, and the yield of $(CF_3CO)_2O$ based on $CF_3COOH$ consumed was 83.4%.

EXAMPLE 8

The first step of the operation was carried out as in Example 7 with the same quantities of reactants and solvent. A first distillate fraction of 182 grams was collected, containing 63% (1.916 moles) of acetic acid.

A second fraction was collected by continuing the distillation up to 131° C. at the head of the column.

The total quantity of $CH_3COOH$ collected represented 1.928 moles, which corresponds to a $(CH_3CO)_2O$ conversion of 96.4%.

After cooling, 912 grams (8 moles) of commercial unredistilled trifluoroacetic acid were added in one portion and the procedure for the distillation of trifluoroacetic anhydride was as in Example 7. There were collected in succession: 152 grams, i.e. 0.723 mole, of $(CF_3CO)_2O$; 758 grams, including 741 grams of $CF_3COOH$ (6.50 moles); and, 18 grams of monochlorobenzene.

In this first cycle, the conversion to $(CF_3CO)_2O$, based on $(CH_3CO)_2O$ employed was thus 72.3% and the yield based on $CF_3COOH$ consumed was 96.4%.

Approximately 190 grams of anhydrous monochlorobenzene were added again to the reactor-boiler to compensate for the quantity removed with the distillates in the first cycle (the first step), followed by 102 grams of pure $(CH_3CO)_2O$ (1 mole).

The procedure was as in the first cycle and two distillate fractions were obtained, the first of 175 grams containing 104 grams of $CH_3COOH$, i.e. 1.733 moles, the second of 100 grams, containing 11 grams of $CH_3COOH$, i.e. 0.183 mole.

The total amount of $CH_3COOH$ leaving the system thus represented 1.916 moles.

To carry out the second step of the operation, 735 grams were added, taken from the batch of 758 grams containing the excess $CF_3COOH$ from the preceding cycle, corresponding to 6.3 moles, and 193.5 grams of $CF_3COOH$ taken from a batch of commercial product, i.e. 1.7 moles. The procedure then continued as described previously. There were then separated off by distillation: 189 grams, i.e. 0.90 mole, of $(CF_3CO)_2O$; and, 701 grams, i.e. 6.14 moles, of $CF_3COOH$.

During this second cycle, the conversion to $(CF_3CO)_2O$ collected, based on $(CH_3CO)_2O$ employed, represented 90%, and its yield based on $CF_3COOH$ converted was 96.7%.

EXAMPLE 9

The procedure was as in Example 7 with dichloroacetic acid being replaced by 239 grams (i.e. 2.2 moles) of α-chloropropionic acid. The mixture was heated at reflux and the head temperature became steady at 112°–113° C. 197 Grams of liquid were then distilled off and collected over 6 hours, from which 111 grams of $CH_3COOH$ were extracted. A 51 gram fraction was then collected (stopped at 130° C. at the head) containing, according to assay, 8 grams of $CH_3COOH$.

After the liquid remaining in the flask had cooled to approximately 70° C., 912 grams of anhydrous $CF_3COOH$, i.e. 8 moles, were added.

The procedure was as in the preceding examples and, over 7 hours, 95 grams of $(CF_3CO)_2O$ coming over at 39.5° C. were collected; a 34 gram fraction of the same component was then separated off over a further 5 hours. The total quantity of trifluoroacetic anhydride recovered was 129 grams (0.614 mole). 750 Grams of $CF_3COOH$ (6.58 moles) were then recovered. The consumption of $CF_3COOH$ was thus (8−6.58 moles) i.e. 1.42 moles and the yield of $(CF_3CO)_2O$ based on $CF_3COOH$ consumed was 86%.

What is claimed is:

1. A process for the preparation of trifluoroacetic anhydride which comprises reacting trifluoroacetic acid with the anhydride of an α-halogenated acid for a time sufficient to obtain said trifluoroacetic anhydride, wherein the α-halogenated acid anhydride corresponds to formula (I):

$$[Y_1(CY_2Y_3)_n\text{---}CO]_2O \qquad (I)$$

in which
- $Y_1$, $Y_2$ and $Y_3$ may be identical or different and are selected from chlorine, bromine and hydrogen;
- n is an integer equal to 1 or 2; and,
- at least one Y situated at a position α to the CO group is chlorine or bromine.

2. The process as claimed in claim 1, wherein the α-halogenated anhydride is produced by reacting the corresponding acid halide with acetic anhydride.

3. The process as claimed in claim 1, wherein the anhydride corresponds to formula (I) in which n=1 and Y is selected from chlorine and hydrogen.

4. The process as claimed in claim 3, wherein the α-halogenated anhydride is produced by reacting the corresponding acid halide with acetic anhydride.

5. The process as claimed in claim 3, wherein the anhydride is dichloroacetic anhydride.

6. The process as claimed in claim 5, wherein the α-halogenated anhydride is produced by reacting the corresponding acid halide with acetic anhydride.

7. The process as claimed in claim 5, wherein the reaction temperature is between about 80° C. and 115° C.

8. The process as claimed in claim 1, wherein the trifluoroacetic acid is present in molar excess relative to the stoichiometry of the reaction.

9. The process as claimed in claim 8, wherein the molar quantity of trifluoroacetic acid employed is between about 2 and 5 times the stoichiometry of the reaction.

10. The process as claimed in claim 9, wherein the molar quantity of trifluoroacetic acid employed is equal to approximately 4 times the stoichiometry of the reaction.

11. The process as claimed in claim 1, wherein the reaction is carried out at a temperature higher than the boiling point of the reaction mixture.

12. The process as claimed in claim 1, wherein the reaction temperature is between about 80° C. and 115° C.

13. The process as claimed in claim 1, wherein the reaction is carried out at atmospheric pressure.

14. The process as claimed in claim 1, wherein the α-halogenated acid anhydride is produced by reacting the corresponding acid halide with acetic anhydride.

15. A process for the preparation of trifluoroacetic anhydride which comprises in a first step, bringing the halide of an α-halogenated acid into contact with acetic anhydride to prepare an α-halogenated acid anhydride which corresponds to formula (I):

$$[Y_1(CY_2Y_3)_n\text{---}CO]_2O \qquad (I)$$

in which
- $Y_1$, $Y_2$ and $Y_3$ may be identical or different and are selected from chlorine, bromine and hydrogen;
- n is an integer equal to 1 or 2; and,
- at least one Y situated at a position α to the CO group is chlorine or bromine, and separating off both the acetyl halide formed and the excess α-halogenated acid halide, and in a second step reacting the remaining mixture with trifluoroacetic acid for a time sufficient to obtain said trifluoroacetic anhydride.

16. A process for the preparation of trifluoroacetic anhydride which comprises in a first step bringing an α-halogenated acid into contact with acetic anhydride in the presence of monochlorobenzene to prepare an α-halogenated acid anhydride which corresponds to formula (I):

$$[Y_1(CY_2Y_3)_n\text{---}CO]_2O \qquad (I)$$

in which
- $Y_1$, $Y_2$ and $Y_3$ may be identical or different and are selected from chlorine, bromine and hydrogen;
- n is an integer equal to 1 or 2; and,
- at least one Y situated at a position α to the CO group is chlorine or bromine, and separating off the azeotrope formed by acetic anhydride and monochlorobenzene, and in a second step reacting the remaining mixture with trifluoroacetic acid for a time sufficient to obtain said trifluoroacetic anhydride.

* * * * *